US008025662B2

United States Patent
Knisely et al.

(10) Patent No.: US 8,025,662 B2
(45) Date of Patent: Sep. 27, 2011

(54) BIDIRECTIONAL REAMING CUTTER

(75) Inventors: Brad Knisely, Warsaw, IN (US); Tamela Garber, Milford, IN (US)

(73) Assignee: Symmetry Medical, Inc., Warsaw, IN (US)

( * ) Notice: Subject to any disclaimer, the term of this patent is extended or adjusted under 35 U.S.C. 154(b) by 794 days.

(21) Appl. No.: 11/090,719

(22) Filed: Mar. 25, 2005

(65) Prior Publication Data
US 2005/0283160 A1 Dec. 22, 2005

Related U.S. Application Data

(60) Provisional application No. 60/556,347, filed on Mar. 25, 2004.

(51) Int. Cl.
*A61B 17/00* (2006.01)
*A61B 17/16* (2006.01)

(52) U.S. Cl. ............. 606/80; 606/79; 408/227; 408/229

(58) Field of Classification Search .............. 606/79–81; 433/165–166; D15/139; 408/227, 229
See application file for complete search history.

(56) References Cited

U.S. PATENT DOCUMENTS

| 4,560,308 | A | * | 12/1985 | Deller | 407/53 |
| 4,706,659 | A | | 11/1987 | Matthews et al. | 128/92 |
| 4,751,922 | A | | 6/1988 | DiPietropolo | 128/92 |
| 5,390,750 | A | * | 2/1995 | Deken et al. | 175/406 |
| 6,221,076 | B1 | | 4/2001 | Albrektsson et al. | |
| 6,238,398 | B1 | | 5/2001 | Lechot | 606/80 |
| 6,258,093 | B1 | * | 7/2001 | Edwards et al. | 606/80 |
| 6,431,801 | B2 | * | 8/2002 | Vasudeva et al. | 408/211 |
| 6,447,518 | B1 | | 9/2002 | Krause et al. | 606/80 |

OTHER PUBLICATIONS

"Design and Evaluation of a New Intramedullary Reamer", William R. Krause, Ph.D.

* cited by examiner

*Primary Examiner* — Eduardo C Robert
*Assistant Examiner* — Julianna N Harvey
(74) *Attorney, Agent, or Firm* — Taylor IP, P.C.

(57) ABSTRACT

A surgical rotary reamer including a shaft and a cutting head connected to the shaft. The cutting head has a plurality of cutting teeth. At least one cutting tooth has a forward portion, a rearward portion and a mid-portion therebetween. The forward portion has a first cutting edge that cuts in a first rotary direction. The rearward portion has a second cutting edge that cuts in the first rotary direction and/or a second rotary direction. The mid-portion interconnects the forward portion and the rearward portion and includes a recessed portion.

18 Claims, 2 Drawing Sheets

BIDIRECTIONAL REAMING CUTTER

CROSS REFERENCE TO RELATED APPLICATIONS

This is a non-provisional application based upon U.S. provisional patent application Ser. No. 60/556,347, entitled "BIDIRECTIONAL REAMING CUTTER", filed Mar. 25, 2004.

BACKGROUND OF THE INVENTION

1. Field of the Invention

The present invention relates to a surgical cutting device, and, more particularly, to a rotary surgical cutting device.

2. Description of the Related Art

Cutters and reamers are used in surgical procedures to prepare canals in bone material to receive implants. The cutters and reamers generally have a hemispherical or cylindrical cutting head. This head is often fixed to the end of a shaft for rotatably driving the cutting head.

An orthopaedic reamer is used to cut a bone and thereby form the interior of the bone into a predetermined shape for receiving an orthopaedic implant. For example, an intramedullary (IM) reamer may be placed into the intramedullary canal of the bone and used to ream the interior of the bone to receive the stem of an orthopaedic implant. Such a reamer includes a radial, peripheral surface which generally includes a plurality of radially extending teeth for cutting the bone in a radial direction as the reamer proceeds in an axial direction into the bone. The size of the opening formed in the bone is determined by the outside diameter of the reamer.

An orthopaedic reamer may also include a cutting head with a distal face which has a plurality of cutting teeth formed therein. The distal face has a shape which corresponds to the shape of an orthopaedic implant to be received within the bone, and includes a plurality of cutting teeth extending from the distal face. The reamer is placed against the bone surface to be cut, such as an acetabulum or glenoid, and is plunge cut into the bone. Such reamers are effective for removing a portion of the bone so that the bone is shaped to receive the implant.

An orthopaedic reamer including a distal face as described above may include cutting teeth which are formed by a punching operation for each individual tooth. Each cutting tooth typically includes a hole and a raised portion which extends from the distal face. The raised portion includes a humped or center portion which results in the bone being cut with an annular groove as the cutting head is rotated about its rotational axis. In other words, each cutting tooth includes a raised portion resembling half of a cone split longitudinally, with the base edge of the cone defining the cutting edge. Although such a cutting tooth configuration is effective to remove the bone for receiving an implant, the rough surface resulting from the cutting teeth may not be desirable for certain applications.

IM reamers typically include an axial cutting face and peripheral fluted cutting teeth. Such reamers can be cylindrical or bullet shaped with multiple cutting flutes along the surface extending from the leading tip. The cutting flutes are oriented with the long axis at a low angle or a helix. Flutes are generally shallow and can become clogged with cutting debris. The cutting work in the bone wall has the affect of forming bone chips, which mixes with other matter in the bone. The rotation of the reamer along with the bone chips and debris may cause heating in the bone that can lead to thermalnecrosis of the bone.

What is needed in the art is a reamer that leaves a smooth cut surface with minimal impact on the bone structure.

SUMMARY OF THE INVENTION

The present invention provides a bidirectional surgical reamer with reduced frictional characteristics.

The present invention comprises, in one form thereof, a surgical rotary reamer including a shaft and a cutting head connected to the shaft. The cutting head has a plurality of cutting teeth. At least one cutting tooth has a forward portion, a rearward portion and a mid-portion therebetween. The forward portion has a first cutting edge that cuts in a first rotary direction. The rearward portion has a second cutting edge that cuts in the first rotary direction and/or a second rotary direction. The mid-portion interconnects the forward portion and the rearward portion and includes a recessed portion.

An advantage of the present invention is that there is reduced friction between the reamer and the bone thereby reducing the temperature of the cutting operation.

Another advantage of the present invention is that cutting is performed bidirectionally both rotationally and axially.

Yet another advantage of the present invention is that the reduced temperature of the reamer reduces thermalnecrosis of the bone.

Still another advantage of the present invention is that the cutting edge on the back of the cutting teeth improve removal and cleanup of the canal upon exiting from the bone.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
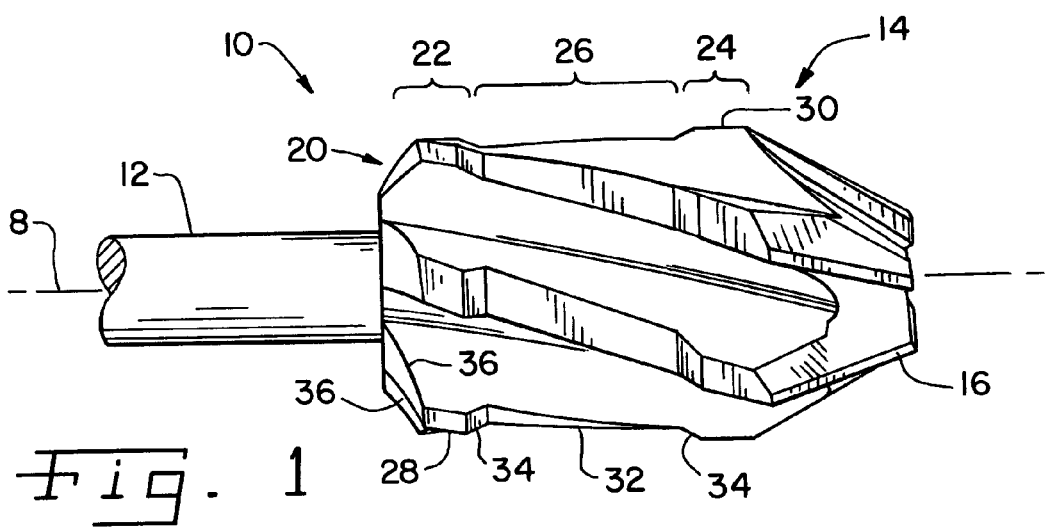
FIG. 1 is a side view of an embodiment of a bidirectional reamer of the present invention.
Figure 2:
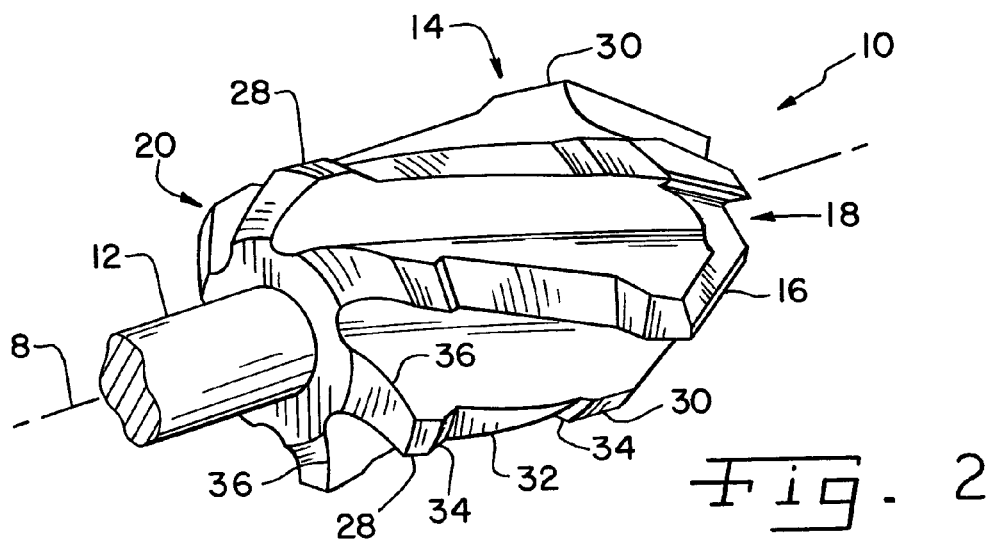
FIG. 2 is a perspective view of the bidirectional reamer of FIG. 1.
Figure 3:
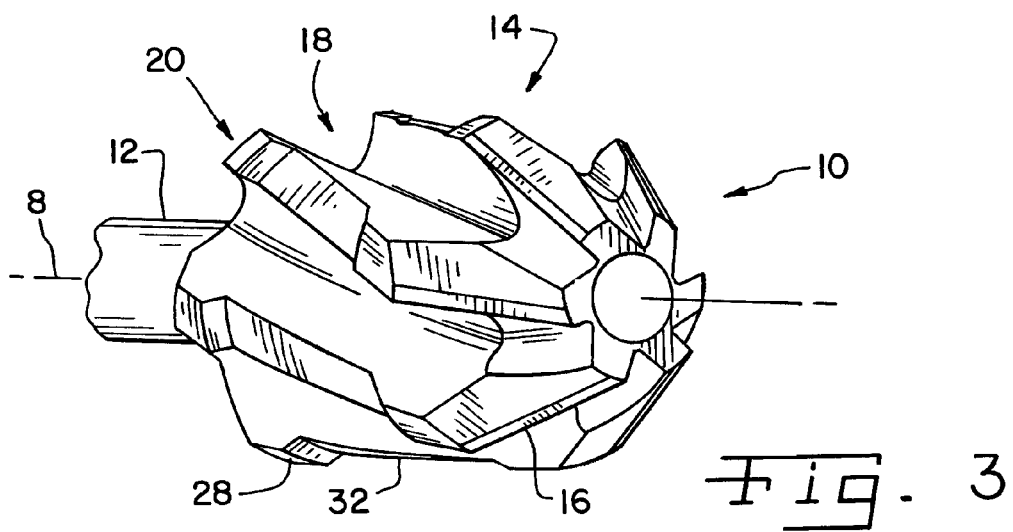
FIG. 3 is yet another perspective view of the reamer of FIGS. 1 and 2.
Figure 4:
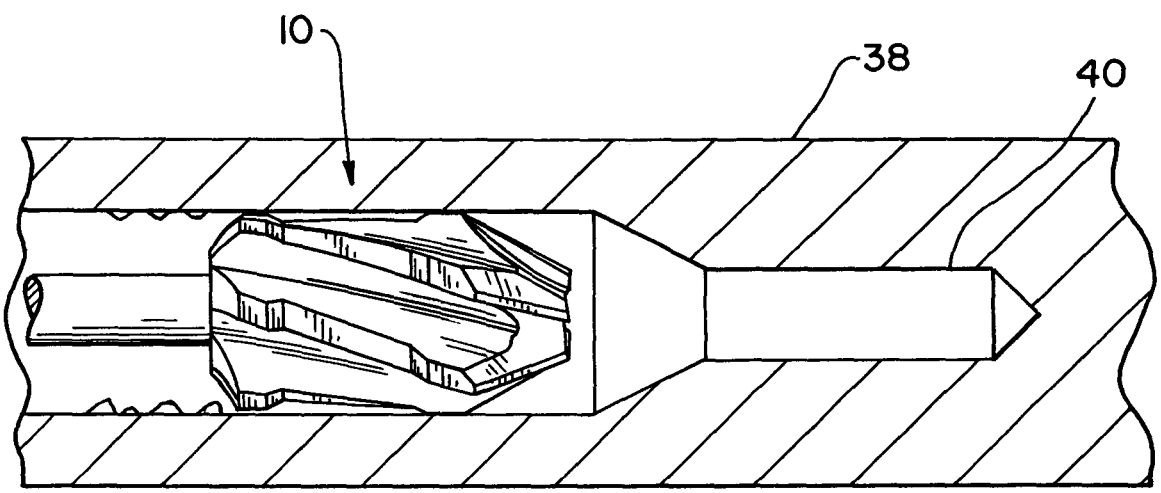
FIG. 4 is a side view of the bidirectional reamer of FIGS. 1-3 in the process of being utilized in a sectional view of a bone.

Referring now to the drawings, and more particularly to FIGS. 1-4, there is shown an embodiment of a bidirectional reamer 10 including a hybrid flexible shaft 12 and a cutting head 14. An end of hybrid flexible shaft 12 is rotationally connected to cutting head 14 along axis 8 and provides rotational torque to cutting head 14 from a rotary power source, not shown. While described as a flexible shaft 12, shaft 12 may be of an alternate configuration, such as solid or jointed.

Cutting head 14 includes forward cutting edges 16, reverse cutting edges 36, flutes 18 and cutting teeth 20. Flutes 18 are the valleys between cutting teeth 20 and flutes 18 are generally equidistant from axis 8 and more particularly spirally equidistant from axis 8. There is defined a rear reamer portion 22, a forward reamer portion 24 and a mid reamer portion 26. Rear reamer portion 22 and forward reamer portion 24 include extended cutting teeth 28 and 30, which extend substantially the same distance from axis 8. Over at least a part of mid-reamer portion 26, cutting teeth 20 extend from axis 8 a reduced dimension as compared with rear reamer portion 22 and forward reamer portion 24, thereby defining a recessed portion 32. More specifically, extended cutting teeth 28 and 30, which are respectively associated with rear reamer portion 22 and forward reamer portion 24, include edges along their periphery shaped so as to provide a cutting edge for the removal of bone material as bidirectional reamer 10 rotates. Additionally, reverse cutting edges 36 assist in the removal of bone material, which may be fragmented during an initial inserting cutting operation. When bidirectional reamer 10 rotates in a clockwise direction, as viewed from the end of shaft 12, forward cutting edges 16 effectively cut into the bone material. When bidirectional reamer 10 rotates in a counter-clockwise direction reverse cutting edges 36 effectively remove material as bidirectional reamer 10 is retracted from the bone.

Extended cutting teeth 28 and 30 are substantially the same distance from axis 8 and are separated by recessed portion 32 having a reduced diameter or distance from axis 8. Transitional portions 34 extend from recessed portion 32 to extended cutting teeth 28 and 30, in an angular fashion from the reduced diameter associated with recessed portion 32 to the distance associated with extended cutting teeth 28 and 30. Although transitional portions 34 have been described as an angular transition a more abrupt or less abrupt transition is also contemplated. The transitional cutting tooth portion 34 associated with extended cutting tooth 28 is substantially a mirror image of transitional cutting tooth portion 34 associated with extended cutting tooth 30. Alternatively, extended cutting teeth 28 may extend a lesser distance from axis 8 than extended cutting teeth 30, thereby causing the cutting edge on extended cutting teeth 30 to be the final cutting portion in contact with bone 38 as bidirectional reamer 10 is withdrawn from bone 38.

As power is supplied by way of shaft 12 to cutting head 14, forward cutting edges 16 remove bone material as bidirectional reamer 10 is inserted into bone 38. Optionally bidirectional reamer 10 may follow a pilot hole 40 cut by another instrument. As bidirectional reamer 10 is advanced in bone 38, material cut by forward cutting edges 16 and edges associated with extended cutting teeth 28 and 30, the spiral shaped flutes allow for the passing of bone material toward rear reamer portion 22. Advantageously, the surfaces of extended cutting teeth 28 and 30 are separated by mid reamer portion 26 to reduce the amount of contact with bone 38, which results in reduced temperature generation in bone 38 as bidirectional reamer 10 rotates therein. As bidirectional reamer 10 is removed from the bone cavity, cutting edges associated with the surfaces of extended cutting teeth 28 and 30 clean up the bone cavity and reverse cutting edges 36 remove any larger material which may have temporarily bonded to a portion of the newly formed cavity or from material shifting in bone 38.

Advantageously, use of the present invention allows for reduced cutting temperatures in the bone canal, which reduces thermalnecrosis of the bone that is experienced with other cutting devices. The resulting bone canal readily accepts a surgical implant into bone 38, which has been altered to a reduced degree because of the reduced cutting temperatures achievable with the present invention.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A surgical rotary reamer, comprising:
   a shaft having an end;
   a cutting head connected to said shaft end, said cutting head having a plurality of cutting teeth, at least one said cutting tooth having:
   only two extended cutting teeth, said two extended cutting teeth being a first extended cutting tooth and a second extended cutting tooth;
   only one recessed portion extending between said first and second extended cutting teeth, said recessed portion being elongate;
   a forward portion having a first cutting edge that cuts in a first rotary direction along a first axial direction and said first extended cutting tooth coupled therewith;
   a rearward portion having a second cutting edge that cuts in a second rotary direction along a second axial direction opposite said first axial direction and said second extended cutting tooth coupled therewith; and
   a mid-portion interconnecting said forward portion and said rearward portion, said mid-portion having only two transitional cutting tooth portions and only one said recessed portion, said recessed portion being between said transitional cutting tooth portions, said recessed portion including a first end and a second end opposing said first end, said first and second ends respectively connected to said transitional cutting tooth portions, said cutting head being coaxially connected to said shaft about an axis of the reamer, said recessed portion being substantially parallel with said axis running from said first end to said second end, said recessed portion having a length which is greater than said first extended cutting tooth and is greater than said second extended cutting tooth.

2. The reamer of claim 1, wherein each of said plurality of cutting teeth are configured substantially identical.

3. The reamer of claim 1, wherein said recessed portion is approximately equidistant a first distance from said axis.

4. The reamer of claim 3, wherein said first extended cutting tooth is a second distance from said axis and said second extended cutting tooth is a third distance from said axis, said first distance being less than said second distance, said first distance being less than said third distance.

5. The reamer of claim 4, wherein said third distance is one of approximately equal to said second distance and less than said second distance.

6. The reamer of claim 5, wherein said second distance and said third distance are approximately equal.

7. The reamer of claim 6, wherein said two transitional cutting tooth portions include a first transitional cutting tooth portion and a second transitional cutting tooth portion, said first transitional cutting tooth portion being between said recessed portion and said first extended cutting tooth, and said second transitional cutting tooth portion being between said recessed portion and said second extended cutting tooth, said first and second transitional cutting tooth portions varying in distance from said axis between said first distance and said second distance.

8. The reamer of claim 7, wherein said first transitional cutting tooth portion is substantially a mirror image of said second transitional cutting tooth portion.

9. A surgical reamer having a plurality of cutting teeth, at least one of the cutting teeth comprising:
   only two extended cutting teeth, said two extended cutting teeth being a first extended cutting tooth and a second extended cutting tooth;
   only one recessed portion extending between said first and second extended cutting teeth, said recessed portion being elongate;
   a forward portion including a first cutting edge that cuts in a first rotary direction along a first axial direction and said first extended cutting tooth coupled therewith;
   a rearward portion including a second cutting edge that cuts in a second rotary direction along a second axial direction opposite said first axial direction and said second extended cutting tooth coupled therewith; and
   a mid-portion interconnecting said forward portion and said rearward portion, said mid-portion having only two transitional cutting tooth portions and only one said recessed portion, said recessed portion being between said transitional cutting tooth portions, said recessed portion including a first end and a second end opposing said first end, said first and second ends respectively connected to said transitional cutting tooth portions, the reamer including a cutting head having a first cutting head end and a second cutting head end, said cutting head including the plurality of cutting teeth, said cutting head having an axis extending from said first cutting head end to said second cutting head end, said recessed portion being substantially parallel with said axis running from said first end to said second end, said recessed portion having a length which is greater than said first extended cutting tooth and is greater than said second extended cutting tooth.

10. The reamer of claim 9, wherein said axis is a rotational axis, said recessed portion being approximately equidistant a first distance from said rotational axis.

11. The reamer of claim 10, wherein said recessed portion interconnects said first extended cutting tooth and said second extended cutting tooth.

12. The reamer of claim 11, wherein said first extended cutting tooth is a second distance from said axis and said second extended cutting tooth is a third distance from said axis, said first distance being less than said second distance, said first distance being less than said third distance.

13. The reamer of claim 12, wherein said third distance is one of approximately equal to said second distance and less than said second distance.

14. The reamer of claim 13, wherein said second distance and said third distance are approximately equal.

15. A method of cutting a cavity in a bone, comprising the steps of:
   providing a shaft having an end and a cutting head connected to said end of said shaft;
   contacting the bone with said cutting head, said cutting head having a plurality of cutting teeth, at least one said cutting tooth having:
      only two extended cutting teeth, said two extended cutting teeth being a first extended cutting tooth and a second extended cutting tooth;
      only one recessed portion extending between said first and second extended cutting teeth, said recessed portion being elongate;
      a forward portion having a first cutting edge that cuts in a first rotary direction along a first axial direction and said first extended cutting tooth coupled therewith;
      a rearward portion having a second cutting edge that cuts in a second rotary direction along a second axial direction opposite said first axial direction and said second extended cutting tooth coupled therewith; and
      a mid-portion interconnecting said forward portion and said rearward portion, said mid-portion having only two transitional cutting tooth portions and only one said recessed portion, said recessed portion being between said transitional cutting tooth portions; and
   rotating said cutting head in a first rotary direction, said recessed portion including a first end and a second end opposing said first end, said first and second ends respectively connected to said transitional cutting tooth portions, said cutting head being coaxially connected to said shaft about an axis of the reamer, said recessed portion being substantially parallel with said axis running from said first end to said second end, said recessed portion having a length which is greater than said first extended cutting tooth and is greater than said second extended cutting tooth.

16. The method of claim 15, further comprising the steps of:
   stopping said cutting head from rotating in said first rotary direction; and
   rotating said cutting head in said second rotary direction.

17. The method of claim 16, wherein said recessed portion is approximately equidistant a first distance from said axis.

18. The reamer of claim 17, wherein said first extended cutting tooth is a second distance from said axis and said second extended cutting tooth is a third distance from said axis, said first distance being less than said second distance, said first distance being less than said third distance.

* * * * *